United States Patent [19]

Poulose et al.

[11] Patent Number: 5,037,662

[45] Date of Patent: Aug. 6, 1991

[54] ENZYME ASSISTED DEGRADATION OF SURFACE MEMBRANES OF HARVESTED FRUITS AND VEGETABLES

[75] Inventors: Ayrookaran J. Poulose, San Bruno; Matthew Boston, San Carlos, both of Calif.

[73] Assignee: Genencor International Inc., South San Francisco, Calif.

[21] Appl. No.: 370,901

[22] Filed: Jun. 23, 1989

[51] Int. Cl.$^5$ ............................................. A23L 1/212
[52] U.S. Cl. .................................... 426/52; 426/289; 426/302; 426/308; 426/615
[58] Field of Search ................... 426/49, 50, 52, 61, 426/63, 289, 302, 308, 615

[56] References Cited

U.S. PATENT DOCUMENTS

| | | | |
|---|---|---|---|
| 2,474,650 | 6/1949 | Birdseye | 426/52 |
| 3,615,687 | 10/1971 | Mochizuki et al. | 426/52 |
| 3,615,721 | 10/1971 | Silberman | 426/52 |
| 4,364,968 | 12/1982 | Waitman et al. | |
| 4,639,375 | 1/1987 | Tsai | 426/52 |
| 4,762,547 | 8/1988 | Iwasaki et al. | |

FOREIGN PATENT DOCUMENTS

| | | |
|---|---|---|
| 302685A | 2/1989 | European Pat. Off. |
| 255267A1 | 3/1988 | Fed. Rep. of Germany |
| 54-11259 | 1/1979 | Japan ................... 426/52 |
| 57-189658 | 11/1982 | Japan ................... 426/52 |

OTHER PUBLICATIONS

Sommer et al., "Chemical Inactivation of Heat Tolerant Pectolytic Enzymes in Raw Apricots Which Cause Softening of the Canned Produce", J. Amer. Soc. Horti., Sci.: 103 (6), pp. 762-767 (1978).

*Primary Examiner*—Marianne Cintins
*Attorney, Agent, or Firm*—Burns, Doane, Swecker & Mathis

[57] ABSTRACT

The present invention discloses that the water permeability across the surface membrane of harvested fruits and vegetables can be substantially increased by treating such surfaces with a degradation enzyme. The resulting products are not only more easily dehydrated but can be used to incorporate desirable substances into the interior of the treated fruit or vegetable, such as sweeteners, stabilizers, preservatives, flavor enhancers.

36 Claims, No Drawings

ENZYME ASSISTED DEGRADATION OF SURFACE MEMBRANES OF HARVESTED FRUITS AND VEGETABLES

BACKGROUND OF THE INVENTION

1. Field of the Invention

The present invention is directed to enzyme assisted degradation of surface membranes of unmacerated harvested fruits and vegetables. In particular, the present invention utilizes degradation enzymes such as cutinases, lipases, cellulases, pectinases, etc., to degrade one or more of the water insoluble components which comprise part of the surface membrane of the fruits and vegetables. Preferably, the surface of the fruit or vegetable is sufficiently degraded so as to result in an increase in water permeability across the surface membrane of at least 50 percent as compared to untreated surfaces. The increased water permeability across the surface membrane permits more facile delivery of substances such as flavorings, sweeteners, stabilizers, and preservatives to the interior of the fruit or vegetable. Additionally, the increased water permeability allows for the more efficient dehydration of fruits and vegetables.

2. Related Art

The surface membranes of fruits and vegetables contain one or more types of water insoluble components which significantly limit the permeability of water across the membrane. Accordingly, this membrane serves the useful role of preventing the evaporation of liquids contained in fruits and vegetables both prior to and after the harvesting of such fruits and vegetables. On the other hand, the production of dried fruits and vegetables require the evaporation (dehydration) of water from the interior of harvested fruits or vegetables. Harvested fruits and vegetables are dried for a variety of reasons. First and most important, dehydration is a method of fruit preservation. Additionally, certain dried fruits and vegetables, i.e., raisins, prunes, apricots, sundried tomatoes, etc., have desirable properties not present prior to drying. One means commercially utilized for drying fruits and vegetables is by osmosis. However, as noted above, the water insoluble components contained in the surface membranes of fruits and vegetables render the surface not completely permeable to water. Thus, while the membranes of cells of fruits and vegetables (below the surface membrane) are selectively permeable to molecules such as water and are therefore susceptible to osmosis, the surface membranes of harvested fruits and vegetables limit osmosis as a means for effecting dehydration. In particular, such osmotic processes inherently require prolonged dehydration.

Additionally, the lack of significant water permeability across this membrane also interferes with the osmotic transport of either natural or synthetic substances into the interior of the fruit or vegetable. On the other hand, the delivery of substances, such as sweeteners, flavor enhancers, preservatives, stabilizers, etc., into the interior of such products could provide beneficial results.

Certain chemicals such as organic solvents, including methanol, chloromethanes (chloroform, methylene chloride), etc., alkali metal hydroxides, etc., can be used to enhance the water permeability of the surface membrane. However, the use of such chemicals is not desirable because traces of these chemicals are retained in the final product and the subsequent ingestion of these chemicals could pose potential harmful side effects. Worker exposure to these chemicals is undesirable and waste treatment of these chemicals is hazardous and difficult. Furthermore, a growing concern among consumers regarding chemicals in food products makes these products less desirable.

While numerous degradation enzymes are known in the art with some being commercially available, these degradation enzymes are primarily known for their role in fruit and/or vegetable decay. On the other hand, some references disclose the use of enzymes on fruit and/or vegetables for the purpose of providing enhanced protection for the treated product.

For example, European Patent Application No. 302 685A discloses the use of an auxin destroying material on the surface of fruit which reduces the occurrence of russeting on the fruit. Auxin is defined by this reference as chemicals, i.e., indole-3-acetic acid, etc., having common biological properties in plants such as stimulation of cell division, stimulation of shoot growth, control of vascular system differation, control of tissue culture differation, control of apical dominance, etc. The auxin destroying materials include microorganisms or compositions containing purified components thereof which can destroy the auxin by chemical degradation. Presumably, the auxin destroying material generated by these microorganisms is an enzyme.

Likewise, U.S. Pat. No. 4,762,547 as well as U.S. Ser. No. 297,224 filed Jan. 13, 1989 discloses the use of esterases, i.e., degradation enzymes, in combination with a biocide. These references disclose that when the esterase is used in conjunction with a biocide, which can be applied either separately or in combination, the esterase results in enhanced biocide activity. U.S. Pat. No. 4,762,547 speculates that the esterase decomposes the foliar wax (surface membrane) of the plant or the epidermal wax of insects, thereby permitting a larger amount of the biocide to enter the treated plant or insect thus resulting in greater biocide activity. Implicit in these references is the fact that the esterase and biocide are applied to plants prior to harvesting.

However, none of these references disclose the use of esterases on the surface membranes of harvested fruits and vegetables as a means for enhancing the water permeability across this surface.

Accordingly, it is an object of this invention to enhance the water permeability of the surface membrane of harvested fruits and vegetables without the use of chemicals which could pose potential harmful side effects if ingested. Such permeability should preferably be increased by at least 50 percent as compared to untreated surfaces.

It is a further object of this invention to facilitate the dehydration of fruits and vegetables without the need for chemicals which act to enhance the surface membrane's water permeability.

It is still a further object of this invention to facilitate the delivery of desirable substances to the interior of the fruit or vegetable.

These and other objects are achieved by the present invention as evidenced by the attached summary of the invention, detailed description of the invention, examples, and claims.

SUMMARY OF THE INVENTION

The present invention is directed to methods for increasing the water permeability of surface membranes of unmacerated harvested fruits and vegetables. The present invention is also directed to the resulting products obtained from such methods. Thus, in its first method aspect, the present invention is directed to a method for increasing the water permeability across the surface membrane of harvested fruits and vegetables wherein said surface membrane contains one or more types of water insoluble components. The method comprises exposing this surface membrane to a sufficient concentration of a degradation enzyme capable of degrading at least one of said water insoluble components for a sufficient period of time so as to provide an increase in water permeability across the membrane of at least 50 percent as compared to untreated fruit or vegetable.

In another method aspect, the present invention is directed to a method for preparing dehydrated fruits or vegetables from harvested fruits and vegetables wherein said harvested fruits and vegetables have a water activity ($a_w$) of greater than 0.80 and further have a surface membrane which contains one or more types of water insoluble components which method comprises exposing the surface membrane of the harvested fruit or vegetable to a sufficient concentration of a degradation enzyme capable of degrading at least one of the water insoluble components for a sufficient period of time so as to provide an increase in water permeability across the membrane of at least 50 percent as compared to the untreated fruit or vegetable; and dehydrating the fruit or vegetable product so produced under conditions sufficient to reduce its $a_w$ to 0.80 or less.

In another method aspect, the present invention is directed to a method of transporting a natural or synthetic substance into the interior of a harvested fruit or vegetable having a surface membrane which contains one or more types of water insoluble components which comprises exposing the surface membrane of the fruit or vegetable to a sufficient concentration of a degradation enzyme capable of degrading at least one of water insoluble components for a sufficient period of time so as to provide an increase in water permeability across the membrane of at least 50 percent as compared to the untreated fruit or vegetable; and exposing the product so produced with an aqueous solution containing sufficient quantities of natural or synthetic substance(s) for a sufficient period of time so as to allow the substance(s) to be osmotically transported to the interior of the product.

In its first product aspect, the present invention is directed to a modified harvested fruit or vegetable product having a surface membrane containing water insoluble components wherein the membrane has a water permeability across this membrane of at least 50 percent greater than the unmodified product and wherein the modified product is free of permeability enhancing chemicals.

In its second product aspect, the present invention is directed to the modified harvested fruit or vegetable product described above and which additionally contains in the interior thereof a quantity of one or more natural substances in excess of that occurring naturally in the unmodified product.

In yet another product aspect, the present invention is directed to the modified harvested fruit or vegetable product described above and which additionally contains in the interior thereof one or more synthetic substances. Preferably, the synthetic substance is selected from the group consisting of sweeteners, flavor enhancers, preservatives, stabilizers, etc.

DETAILED DESCRIPTION OF THE INVENTION

The present invention is directed to enzyme assisted degradation of surface membranes of harvested fruits and vegetables. In particular, surface membranes of fruits and vegetables contain, in part, one or more types of water insoluble components which significantly limit the permeability of water across this membrane. As a result, the dehydration of or the osmotic delivery of substances into the interior of fruits and vegetables is impaired. Methods disclosed by this invention result in modified fruit and vegetable products having substantially greater permeability to water than unmodified products. As a result, the modified fruit and vegetable products of this invention not only permit the more facile dehydration of these products, such as in the preparation of dried fruits and vegetables, but also permit the osmotic delivery of substances to the interior of these products. Moreover, the products of this invention are free of permeability enhancing chemicals.

Prior to discussing this invention in detail, the following terms will be defined:

"Water insoluble components"—refer to those components which comprise part of the surface membrane of fruits and/or vegetables thereby rendering this surface membrane not completely permeable to water. Such components do not have any significant solubility in water and can comprise polymers such as cutin, cellulose, pectin, etc., as well as water insoluble materials such as triglyercides, wax esters, etc. Other additional water insoluble components are well known in the art.

"Degradation enzymes"—refer to enzymes capable of degrading at least one type of water insoluble components. Suitable degradation enzymes include lipase, cutinase, cellulase, pectinase, etc. Lipase sources include those originating in the genera Candida, Pseudomonas, Rhizopus, Aspergillus, Mucor, etc. Such lipases are capable of degrading the water insoluble triglycerides which can comprise part of the surface membrane. Commercially available products can be used for the present invention.

Cutinase sources include those originating in the genera Pseudomonas, Fusarium, Botrytis, Ulocladium, etc. See, for instance, "Cutinases from Fungi and Pollen", P. E. Kolattukudy, pages 472–504 and which is incorporated herein by reference. A particularly preferred cutinase is one prepared from the genus *Pseudomonas mendocina* ATCC 53552, the isolation and specific amino acid sequence of which is described in U.S. Ser. No. 107,092, filed Oct. 19, 1987, entitled "Novel Hydrolase and Method"; as well as U.S. Ser. No. 297,224, filed Jan. 13, 1989 and entitled "Enzymes as Agricultural Chemical Adjuvants", the disclosure of both of which are incorporated herein by reference in their entirety. Other cutinases can include commercially available products. Such cutinases are capable of degrading the water insoluble cutin polymer which can comprise part of the surface membrane of the fruit or vegetable.

Cellulase sources include those originating in the genera Trichoderma, Penicillum, Aspergillus, Clostridium, etc. Additional cellulases can include commercially available products. Such cellulases are capable of degrading the water insoluble cellulose polymer comprising part of the surface membrane of the fruit or vegetable.

Lipase sources include those originating in the genera Staphylococcus, Candida, Rhizopus, etc. Additional lipases can include commercially available products. Such lipases are capable of degrading the water insoluble gylcerol components comprising part of the surface membrane of the fruit or vegetable.

Pectinase sources include those originating in the genera Rhizopus, Penicillium, Aspergillus. etc. Additional pectinases can include commercially available products. Such pectinases are capable of degrading the water insoluble pectin components comprising part of the surface membrane of the fruit or vegetable.

Also included within the term "degradation enzyme" are two or more degradation enzymes which have been combined, i.e., a lipase combined with a cutinase, etc. Such combinations may provide for degradation capabilities against two or more types of water insoluble components which may be contained in the surface membrane.

"Non-ionic surfactant"—refers to surfactants which have neither a cationic nor an anionic group. Such non-ionic surfactants include Triton TM, especially Triton TM X-100, Span TM, Tween TM, sucrose esters, alkyl glucosides, etc. The particular non-ionic surfactant employed is not critical provided it does not interfere with the enzyme activity of the degradation enzyme.

"Natural substances"—refer to substances which are indigenous to that fruit or vegetable and includes substances such as sugars, antibiotics, etc. produced by that particular fruit or vegetable.

"Synthetic substances"—refer to substances which are not indigenous to that fruit or vegetable but which if included in the interior of the fruit and/or vegetable would provide beneficial results. Such synthetic substances include sweeteners, flavor-enhancers, preservatives, stabilizers, etc. Preferably, the synthetic substance is one which is naturally produced albeit not by that fruit or vegetable, i.e., a substance produced by either an organism or by a different fruit, plant or vegetable.

The term "$a_w$"—refers to water activity and is a measure of the water content in the fruit or vegetable. Fresh fruits typically have water contents greater than 90%, with water activities ($a_w$) of about 0.97. Fruit dried using conventional technology lowers its water content to about 20%, with an $a_w$ from about 0.72 to about 0 80. It is particularly desirable that the $a_w$ of the dried product be lowered to 0.80 or less. This is because bacteria, yeasts, and mold do not grow at an $a_w$ below 0.91, 0.88, and 0.80 respectively. Thus lowering the $a_w$ of the dried product to 0.80 or less, provides for a product not susceptible to spoilage by bacteria, yeasts, and molds. In general, freshly harvested fruits and vegetables to be used in the methods of this invention should have an $a_w$ of greater than 0.80; preferably greater than 0.90; and even more preferably greater than 0.95.

"Permeability enhancing chemicals"—refer to certain chemicals, such as organic solvents, e.g., methanol, chloroform, methylene chloride, etc., alkali metal hydroxides, including sodium hydroxide and potassium hydroxide, which when exposed to the surface membrane enhance its water permeability. Characteristic of such permeability enhancing chemicals is the fact that these chemicals are not naturally produced and may pose potential harmful side effects if ingested. On the other hand, as used herein, the term "permeability enhancing chemicals" does not include degradation enzymes which are naturally produced enzymes, i.e., proteins, which can be transformed when ingested into useful products, i.e., polypeptides and amino acids including essential amino acids.

The methods of the present invention utilize enzyme assisted degradation of one or more of the water insoluble components found in the surface membranes of fruits and vegetables as a means of enhancing the water permeability across this membrane. In general, the surface membrane of a harvested fruit or vegetable is exposed to a sufficient concentration of a degradation enzyme for a sufficient period of time so as to achieve the desired increase in water permeability across the membrane. Because the degradation enzyme's activity is stable over an extended period of time, e.g., for several days at pH 7, it would be anticipated that the concentration of degradation enzyme required to achieve the desired increase in permeability would be inversely proportional to the exposure time. That is to say, if a short exposure time is employed, then higher concentrations of degradation enzyme would be required to achieve the desired permeability. Conversely, if longer exposure times are employed, then the concentration of the degradation enzyme could be proportionally reduced to still arrive at the desired result. While the above correlation is generally true for most enzymes, certain enzymes such as cutinase derived from *Pseudomonas putida* can exhibit reduced activity at concentrations above 0.3 mg/ml. While not being limited to any theory, it is believed that this result arises because of concentration dependent aggregation effects arising in this enzyme. However, any such aggregation can be diminished by using art recognized techniques such as the use of detergents, etc.

With regard to exposure times, the increase in water permeability will initially be linear with exposure time and then asymptotically approach the maximum increase possible. Thus, while the above correlation is generally true for exposures times falling on the linear portion of activity, it is not true for the non-linear (asymptotic) portion. In any event, it is well within the skilled artisan's ability to select the appropriate concentration of degradation enzyme and the appropriate exposure time to arrive at the desired increase in water permeability.

In a preferred embodiment, the degradation enzyme is generally employed at a concentration of at least about 0.01 mg/ml; more preferably, the concentration of degradation enzyme is from about 0.05 mg/ml to about 1.0 mg/ml; and even more preferably at a concentration of from about 0.1 mg/ml to about 0.5 mg/ml.

Also, in a preferred embodiment, the exposure time of the degradation enzyme to the surface membrane of the fruit or vegetable is generally at least one hour; more preferably, the exposure time is from about four hours to about twenty-five hours; and even more preferably from about ten hours to about twenty hours.

The degradation enzyme is generally exposed to the surface membrane of the fruit or vegetable at a temperature sufficiently high for the enzyme to exhibit an acceptable level of activity but not so high as to cause the enzyme to denature. In general, temperatures of from about 10° C. to about 50° C. are acceptable while temperatures of from about 20° C. to about 40° C. are preferred.

In general, the fruit or vegetable is exposed to a sufficient concentration of the degradation enzyme for a sufficient period of time so as to result in an increase in water permeability of at least 50% over untreated fruit or vegetable. Preferably, if the treated fruit or vegetable is to be used to prepare a dried product, then the increase in permeability should be at least about 200%, and more preferably, at least about 1000%. Most preferably, the increase in permeability should be a large as possible in order to speed the dehydration process. On the other hand, if the treated fruit or vegetable is to be used in the process which incorporates natural or synthetic substances into the interior thereof, than preferably the increase in permeability should be from at about 50% to about 500% in order to retain as much of the product's original appearance and texture as is possible.

Preferably, the degradation enzyme is employed in an aqueous solution which can be so selected so as to provide optimum conditions for enzyme activity. Thus factors such as pH, stabilizers, temperatures, buffer content, etc., can be readily maintained or incorporated into the aqueous solution. For example, the pH employed in combination with the degradation enzyme can range from about 4 to 11, with a pH of 10 being preferred when the cutinase is isolated from *Pseudomonas putida*. An appropriate pH can readily be maintained in an aqueous solution by the appropriate choice of buffers. Additionally, the aqueous solution can also contain any necessary substrate required for enzyme activity (if not contained in the vegetable or fruit) as well as stabilizers, scavengers, etc.

In a preferred embodiment, the aqueous solution additionally contains a non-ionic surfactant. While this non-ionic surfactant has little or no effect on dehydration by itself, the combination of the degradation enzyme and the non-ionic surfactant synergistically enhances the amount of water insoluble component degraded by the degradation enzyme (as measured by an increase in dehydration which correlates to surface membrane's water permeability). Without being limited to any theory, this synergy appears may be due to the non-ionic surfactant aiding the degradation enzyme in penetrating the surface membrane, which makes the water insoluble components more available to the degradation enzyme. When so used, the non-ionic surfactant is generally employed in an amount sufficient to enhance the degradation activity of the degradation enzyme. Preferably, the amount of nonionic surfactant employed ranges from about 0.005% to about 0.5% and more preferably, from about 0.01% to about 0.10%.

As before, the surface membrane of the fruit or vegetable is exposed to a sufficient concentration of degradation enzyme for a sufficient period of time so as to result in the desired increase in water permeability. At this time, this product is then subjected to dehydration if a dried product is desired. One method of dehydrating is by osmosis. In osmosis, an aqueous solution containing a sufficient concentration of solute is exposed to the surface membrane of the fruit or vegetable. The amount of solute contained in solution must be greater than its concentration in the fruit or vegetable. Under such conditions, osmosis occurs, i.e., the solute is transported into the fruit or vegetable and water is transported from the fruit or vegetable into the aqueous solution with a net loss of water in the fruit or vegetable. Osmosis will continue until equal concentrations of solute are found on both sides of the surface membrane. Thus, by merely selecting the concentration of solute, one can select the amount of water removed from the fruit or vegetable. Preferably, the solute employed is a natural product such as a sugar, i.e., sucrose, glucose, fructose, etc., glycerol, etc., which, as above, is incorporated into the product. In addition, the solution can contain materials such as vitamins, minerals, etc., which during the course of osmotic dehydration would also be incorporated into the product.

The osmotic conditions selected are not critical as long as they are sufficient to permit osmosis to proceed. For example, the time for which osmosis is allowed to proceed is not critical and is generally governed by the desired degree of dehydration, i.e., osmosis is allowed to proceed until the desired degree of dehydration is reached and then terminated. Likewise, the temperature that the osmosis is conducted at is not critical but temperatures of from about 10° C. to about 40° C. are preferred. Solute concentrations also are not critical but should be selected so as to allow osmosis to continue to at least the point where the desired degree of dehydration has occurred. Additionally, solute concentration is governed by the solute's solubility in solution. Solute concentrations up to its maximum solubility in solution can be used. Lastly, the solute employed must be permeable to the surface membrane. Solutes such as sugars, glycerol, aspartame, vitamins, etc., are suitable. Other suitable solutes are well known in the art. The pH of the solution is also not critical and can range from about 4 to about 11, although certain pH's may be preferred. For example, when cutinase isolated from *Pseudomonas putida* is used as the degradation enzyme, a pH of about 7-10 is preferred with of 10 being optimum for dehydration (osmosis)—possibly due to residual cutinase activity which has an optimal pH of about 10.

Dehydration is generally allowed to continue until the $a_w$ of the product is 0.80 or less. After the desired degree of dehydration has been obtained, the resulting dehydrated product is removed from the osmotic conditions and then is preferably dried to remove residual moisture. The particular drying method is not critical and any suitable drying means can be used, i.e., evaporation, blotting, etc.

Another suitable dehydration method is evaporation which includes sun-drying, heating, etc. For example, in sun-drying, the fruit or vegetable is exposed to sunlight for a suitable length of time to allow a sufficient amount of moisture to be removed by evaporation from the product. Suitable conditions are well known in the art. In any event, by increasing the surface membrane's permeability, it is possible to increase the speed of dehydration whether dehydration is by osmosis, evaporation, etc.

When the product obtained by exposing the surface of the fruit or vegetable to an degradation enzyme is intended to be used for the incorporation of a natural or synthetic substance into the interior of the product, the osmotic conditions described above are equally pertinent here with the following exceptions. Firstly, while the duration of osmosis is still not critical, it is nevertheless substantially shorter than the duration of osmosis in hydration because significant dehydration is not intended and, in fact, not desired. That is because significant dehydration, i.e., water loss of 10% or more from the product, can result in loss of the original appearance and texture of the treated fruit or vegetable. In order to minimize dehydration and change in product appearance and texture, the increase in water permeability across the surface membrane should be kept in the range of at least 50% to about 500% and preferably from about 100% to about 400% as compared to the untreated fruit or vegetable. In any event, the time employed for osmosis is generally a duration sufficient to allow the osmotic transport of the desired quantity of natural of synthetic substance into the interior of the product.

Secondly, the concentration of solute is generally less than in osmotic dehydration in order to minimize dehydration. For example, solute concentrations slightly higher than the concentrations of the solute in the fruit or vegetable, at most about 10 mg/ml higher, allow for incorporation of the solute into the interior of the product without significant dehydration. It is also noted that the concentration of the solute can differ for natural and synthetic substances. In particular, for a natural substance, it is necessary to employ a higher concentration of this substance in the aqueous solution than is found in the product in order for this substance to be transported into the product by osmosis. On the other hand because a synthetic substance is by definition a substance not contained in the product, any concentration of this substance in solution will be greater than that in the product and osmosis will proceed. Selecting the appropriate conditions for osmotically transporting a natural or synthetic substance into the interior of a fruit or vegetable product treated with a degradation enzyme is well within the capabilities of the skilled artisan. The product prepared by osmotically transporting the natural or synthetic substance into the interior of the fruit or vegetable is by necessity free of permeability enhancing chemicals because such chemicals were not used.

The following examples are offered to illustrate the invention and should not be construed in any way as limiting the scope of this invention.

EXAMPLES

In the following examples, recitation of percentages in solution refer to weight percentages. Recitation of tomatoes refer to cherry tomatoes which were purchased locally and selected for their similarity in color, weight and skin quality. Typically groups of five (having a total mass of 100-150 grams) were rinsed and washed and then used in the examples. In Examples 1-7, cutinase refers to the cutinase enzyme isolated from Pseudomonas putida described earlier.

EXAMPLE 1

Tomatoes were incubated in an aqueous solution containing 100 mM glycine buffer and 0.05% sodium azide which optionally contained 0.18 mg/ml cutinase at various pH's for 18 hours at 37° C. They were then washed with water, blotted dry on a paper towel, and placed in an aqueous dehydrating solution containing 50% sucrose, 0.05% sodium azide at a ratio of 1.8 ml of solution per gram of tomato. After 408 hours at room temperature at about pH 7, they were removed, blotted dry, and weighed. [In this and in subsequent examples, solutions containing cutinase are indicated by + (plus); solutions not containing cutinase are indicated by − (minus)]

| pH | cutinase | % weight loss |
|---|---|---|
| 4.6 | − | 13 |
| 4.6 | + | 17 |
| 7.5 | − | 18 |
| 7.5 | + | 21 |
| 10.0 | − | 21 |
| 10.0 | + | 33 |

The above data demonstrates that incubation with cutinase increases the % weight loss at all pH's tested. However, the above data also demonstrates that higher pH increases the % of weight loss, and the two exhibit a concerted effect.

EXAMPLE 2

A. Tomatoes were incubated in an aqueous solution containing 0.16 mg/ml cutinase, 100 mM glycine, 0.05% sodium azide at pH 10, for 18 hours at 22° C. They were then washed with water blotted dry on a paper towel, and placed in an aqueous dehydrating solution containing 50% glycerol, 100mM glycine, 0.05% sodium azide buffered to various pH's at a ratio of 1.8 ml/g tomato. After 508 hours at 22° C., they were removed, blotted dry, and weighed.

| pH | cutinase | % weight loss |
|---|---|---|
| 7.0 | + | 33 |
| 10.0 | + | 35 |

B. In a similar treatment as A above, tomatoes were incubated in the same aqueous solution optionally containing cutinase (0.16 mg/ml) but for 18 hours at 37° C. They were then washed with water, blotted dry and placed in the same dehydrating medium under the same conditions but at varying pH's. After 144 hours at 22° C., the tomatoes were removed, blotted dry, and weighed.

| pH | cutinase | % weight loss |
|---|---|---|
| 8.0 | − | 12 |
| 8.0 | + | 16 |
| 10.0 | − | 11 |
| 10.0 | + | 21 |

C. In a similar treatment as A above, tomatoes were incubated for the same length of time in the same aqueous solution containing cutinase at the same temperature. They were then washed with water, blotted dry on a paper towel and placed in an aqueous dehydrating solution containing 25% glucose, 100 mM glycine, 0.05% sodium azide, at a ratio of 1.8 ml solution per gram of tomato. After 508 hours at 22° C., the tomatoes were removed, blotted dry, and weighed.

| pH | cutinase | % weight loss |
|---|---|---|
| 7.0 | + | 19 |
| 8.0 | + | 17 |
| 9.0 | + | 12 |
| 10.0 | + | 21 |

EXAMPLE 3

Tomatoes were incubated for 18 hours at 37° C. in 100 mM glycine, pH 10, 0.5% sodium azide and two different cutinase concentrations. They were then washed, blotted dry, and placed in an aqueous dehydrating solution containing 50% sucrose, 100 mM glycine, 0.05% sodium azide at pH 10 and at 22° C. A ratio of 1.8 ml/gram of tomato was maintained throughout. After 408 hours, they were removed and weighed.

| cutinase concentration | % weight loss |
|---|---|
| 0.18 mg/ml | 33 |
| 0.36 mg/ml | 15 |

Without being limited by an theory, it is believed that the decrease in weight loss with increasing cutinase concentration could be the result of concentration dependent aggregation effects.

EXAMPLE 4

Tomatoes were incubated with 0.16 mg/ml cutinase, 100 mM glycine, pH 10, 0.05% sodium azide for 18 and 40 hours at 37° C. They were then washed, blotted dry and placed in an aqueous dehydrating solution containing 100 mM glycine, 50% glycerol, 0.05% azide solution at pH 10 and a ratio of 1.8 ml of dehydrating solution per gram of tomato was maintained throughout. After 144 hours at 22° C., they were removed and weighed.

| 18 hours | 21% weight loss |
|---|---|
| 40 hours | 20% weight loss |

The above data indicates that under these conditions, the maximum increase in permeability to the surface membrane was reached within the first 18 hours of exposure to cutinase.

EXAMPLE 5

Tomatoes were incubated in an aqueous solution containing 100 mM glycine, 0.05% sodium azide and optionally 0.16 mg/ml cutinase and 0.01 or 0.02% sodium dodecylsulfate at pH 10 and at 37° C. for 18 hours. After incubation, the tomatoes were washed, blotted dry with a paper towel and added to an aqueous dehydrating solution containing 50% glycerol, 100 mM glycine, 0.05% sodium azide at pH 10 and at 22° C. for 144 hours at a ratio of 1.8 ml of solution per gram of tomato. Afterwards, the tomatoes were removed, blotted dry and weighed. The different solutions used are set forth in Table II below:

TABLE II

|  | Solutions | | | | | |
|---|---|---|---|---|---|---|
|  | I | II | III | IV | V | VI |
| cutinase[a] | − | + | − | − | + | + |
| 0.01% SDS[b] | − | − | + | − | + | − |
| 0.02% SDS[b] | − | − | − | + | − | + |

The results of this test are set forth in Table III below.

TABLE III

|  | Solutions (% weight loss) | | | | | |
|---|---|---|---|---|---|---|
| hours | I | II | III | IV | V | VI |
| 144 | 11 | 21 | 12 | 13 | 21 | 22 |

The above results show that an ionic surfactant does not have any significant effect on the dehydration of the tomatoes.

EXAMPLE 6

The procedure set forth in Example 5 was followed except that a non-ionic surfactant, TRITON X-100, was used in place of SDS and the tomatoes were weighed during a time course of 16, 40 and 144 hours. The different solutions used are set forth in Table IV below:

TABLE IV

|  | Solution | | | | | |
|---|---|---|---|---|---|---|
|  | VII | VIII | IX | X | XI | XII |
| cutinase[a] | − | + | − | − | + | + |
| TRITON X-100 (0.01%) | − | − | + | − | + | − |
| TRITON X-100 (0.02%) | − | − | − | + | − | + |

The results of this test are set forth in Table V below:

TABLE V

|  | Solution (% weight loss) | | | | | |
|---|---|---|---|---|---|---|
| hours | VII | VIII | IX | X | XI | XII |
| 16 | − | − | 2 | 1 | 24 | 30 |
| 40 | − | − | 5 | 3 | 37 | 41 |
| 144 | 11 | 21 | 14 | 11 | 40 | 45 |

The above data demonstrates that within 40 hours, over 40% of the weight of the tomatoes treated with solution XII was lost, while the tomatoes treated with solution X lost 3% of their weight in the same amount of time. Likewise, tomatoes treated with solution VIII lost 21% of their weight but over 144 hours. While the non-ionic surfactant had little effect on dehydration by itself, the above data also demonstrates that there is more than an additive effect when both the cutinase and non-ionic surfactant are used together.

By following the procedures set forth above in Examples 1-7 above, other fruits and vegetables such as grapes, apricots, plums, apples, etc., could be substituted for tomatoes to achieve a dehydrated product. Likewise, other degradation enzymes, such as lipases, pectinases, cellulases, etc., could be substituted for cutinase to achieve a dehydrated product.

EXAMPLE 8

Tomatoes are rinse, weighed, and incubated in an aqueous solution containing 100 mM glycine, 0.05% sodium azide and 0.10 mg/ml of pectinase isolated from Aspergillus at pH 10 for 3 hours at 22° C. The tomatoes are then washed with water, blotted dry, and placed in an aqueous solution containing 1% of aspartame (a sweetner), 100 mM glycine, and 0.05% sodium azide at a ratio of 1.8 ml of solution to gram of tomato. After 48 hours, the tomatoes are removed and blotted dry. The above procedure permits the incorporation of a sweetner into the tomato with minimal dehydration. By following the above procedure, other substances such as preservatives, stabilizers, color enhancers, etc., could be substituted for tomatoes to achieve a product having this substance incorporated into the interior thereof. Likewise, other degradation enzymes, such as lipase, cellulase, cutinase, etc., could be substituted for pectinase to achieve a modified product.

What is claimed is:

1. A method for increasing the permeability of water across the surface membrane of unmacerated harvested fruits and vegetables wherein said surface membrane contains one or more types of water insoluble components selected from the group consisting of cutin, cellulose, pectin, triglycerides and waxy esters, said method comprises exposing said surface membrane to a composition comprising a sufficient concentration of a degradation enzyme selected from the group consisting of lipase, cutinase, cellulase, and pectinase and a sufficient concentration of a non-ionic surfactant so as to enhance the activity of said degradation enzyme for a sufficient period of time so as to provide for an increase in water permeability across said membrane of at least fifty percent as compared to the water permeability of said harvested fruits and vegetables prior to exposure to said composition.

2. The method according to claim 1 wherein the increase in water permeability across said membrane is at least two hundred percent.

3. The method according to claim 2 wherein the increase in water permeability across said membrane is at least one thousand percent.

4. The method according to claim 1 wherein said degradation enzyme is contained in an aqueous solution.

5. The method according to claim 4 wherein the concentration of said degradation enzyme in said aqueous solution is at least 0.01 mg/ml.

6. The method according to claim 4 wherein said surface is exposed to said aqueous solution containing said degradation enzyme for a period of at least one hour.

7. The method according to claim 5 wherein the concentration of said non-ionic surfactant in said aqueous solution is at least 0.005 percent by weight.

8. The method according to claim 7 wherein said non-ionic surfactant is selected from the group consisting of Triton TM, Span TM, Tween TM, and sucrose esters.

9. The method according to claim 7 wherein said non-ionic surfactant is Triton X-100.

10. The method according to claim 1 wherein the degradation enzyme is selected from the group consisting of cutinases and lipases.

11. The method according to claim 1 wherein said degradation enzyme is cutinase isolated from *Pseudomonas mendocina*.

12. A method for preparing dehydrated fruits and vegetables from unmacerated harvested fruits and vegetables wherein said harvested fruits and vegetables have a water activity ($a_w$) of greater than 0.80 and further have a surface membrane which contains one or more types of water insoluble components selected from the group consisting of cutin, cellulose, pectin, triglycerides and waxy esters, which method comprises:
(a) exposing the surface membrane of said harvested fruit or vegetable to a composition comprising a sufficient concentration of a degradation enzyme selected from the group consisting of cutinase, cellulase, pectinase and lipase and a non-ionic surfactant at a concentration sufficient to enhance the activity of said degradation enzyme for a sufficient period so as to provide for an increase in water permeability across said membrane of at least fifty percent as compared to said fruits and vegetables prior to exposure to said composition; and
(b) dehydrating the fruit or vegetable product produced by step (a) above under conditions sufficient to reduce its $a_w$ to 0.80 or less.

13. The method according to claim 12 wherein the increase in water permeability across said membrane is at least one thousand percent.

14. The method according to claim 12 wherein said degradation enzyme is contained in an aqueous solution.

15. The method according to claim 14 wherein the concentration of said degradation enzyme in said aqueous solution is at least 0.01 mg/ml.

16. The method according to claim 15 wherein said surface is exposed to said aqueous solution containing said degradation enzyme for a period of at least one hour.

17. The method according to claim 12 wherein the concentration of said non-ionic surfactant in said aqueous solution is at least 0.005 percent by weight.

18. The method according to claim 12 wherein said non-ionic surfactant is selected from the group consisting of Triton TM, Span TM, Tween TM, and sucrose esters.

19. The method according to claim 12 wherein said non-ionic surfactant is Triton X-100.

20. The method according to claim 12 wherein said degradation enzyme is selected from the group consisting of cutinases and lipases.

21. The method according to claim 12 wherein said degradation enzyme is cutinase isolated from *Pseudomonas mendocina*.

22. The method according to claim 12 wherein said dehydrating step is selected from the group consisting of osmosis and evaporation.

23. The method according to claim 22 wherein said dehydrating step is an osmotic dehydration.

24. The method according to claim 23 which further comprises drying the dehydrated product produced in step (b) to remove at least one of the residual moisture.

25. A method of transporting a natural or synthetic substance into the interior of an unmacerated harvested fruit or vegetable having a surface membrane which contains one or more types of water insoluble components selected from the group consisting of cutin, cellulose, pectin, triglycerides and waxy esters, which method comprises:
(a) exposing the surface membrane of said fruit or vegetable to a composition comprising a sufficient concentration of a degradation enzyme selected from the group consisting of cutinase, cellulase, pectinase, and lipase and a sufficient concentration of a non-ionic surfactant so as to enhance the activity of said degradation enzyme for a sufficient period of time so as to provide an increase in water permeability across said membrane of at least 50 percent as compared to the water permeability of said harvested fruit or vegetable prior to exposure to said composition; and
(b) exposing the product produced by step (a) above with an aqueous solution containing sufficient quantities of natural and/or synthetic substance(s) for a sufficient period of time so as to allow said substance(s) to be osmotically transported to the interior of said product.

26. The method according to claim 25 wherein the increase in permeability across said membrane is from at least 100 percent to about 400 percent.

27. The method according to claim 26 wherein said degradation enzyme is contained in an aqueous solution.

28. The method according to claim 27 wherein the concentration of said degradation enzyme in said aqueous solution is at least 0.01 mg/ml.

29. The method according to claim 28 wherein said surface is exposed to said aqueous solution containing said degradation enzyme for a period of at least one hour.

30. The method according to claim 28 wherein the concentration of said non-ionic surfactant in said aqueous solution is at least 0.005 percent by weight.

31. The method according to claim 30 wherein said non-ionic surfactant is selected from the group consisting of Triton ™, Span ™, Tween ™, and sucrose esters.

32. The method according to claim 30 wherein said non-ionic surfactant is Triton X-100.

33. The method according to claim 25 wherein said degradation enzyme is selected from the group consisting of cutinases and lipases.

34. The method according to claim 25 wherein said degradation enzyme is cutinase isolated from Pseudomonas mendorina.

35. The method according to claim 25 wherein said substance is a natural substance.

36. The method according to claim 25 wherein said substance is a synthetic substance.

* * * * *

UNITED STATES PATENT AND TRADEMARK OFFICE
CERTIFICATE OF CORRECTION

PATENT NO. : 5,037,662

DATED : August 6, 1991

INVENTOR(S) : Ayrookaran J. Poulose and Matthew Boston

It is certified that error appears in the above-identified patent and that said Letters Patent is hereby corrected as shown below:

Column 3, line 43, after "at least one of" insert --the--.

Column 4, lines 42 and 43, where "Candida, Pseudomonas, Rhizopus, Aspergillus, Mucor" should read --Candida, Pseudomonas, Rhizopus, Aspergillus, Mucor--; line 49, where "Pseudomonas, Fusarium, Botrytis, Ulocladium" should read --Pseudomonas, Fusarium, Botrytis, Ulocladium--; and lines 66 and 67, where "Trichoderma, Penicillum, Aspergillus, Clostridium" should read --Trichoderma, Penicillium, Aspergillus, Clostridium--.

Column 5, line 5, where "Staphylococcus, Candida, Rhizopus" should read --Staphylococcus, Candida, Rhizopus--; line 11, where "Rhizopus, Penicillium, Aspergillus." should read --Rhizopus, Penicillium, Aspergillus--; lines 25 and 26, where "Triton TM, especially Triton TM X-100, Span TM, Tween TM" should read --Triton$^{TM}$, especially Triton$^{TM}$ X-100, Span$^{TM}$, Tween$^{TM}$--and line 49, delete "0 80" and insert in place thereof --0.80--.

Column 6, lines 30 and 31 where "Pseudomonas putida" should read --Pseudomonas mendocina--; and line 42, delete "exposures" and insert in place thereof --exposure--.

UNITED STATES PATENT AND TRADEMARK OFFICE
CERTIFICATE OF CORRECTION

PATENT NO. : 5,037,662

DATED : August 6, 1991

INVENTOR(S) : Ayrookaran J. Poulose and Matthew Boston

It is certified that error appears in the above-identified patent and that said Letters Patent is hereby corrected as shown below:

Column 7, line 13, delete "than" and insert in place thereof --then--; lines 25 and 26, where "Pseudomonas putida" should read --Pseudomonas mendocina--; line 39, after "which correlates to" insert --the--; and line 41, delete "appears".

Column 8, lines 30 and 31, where "Pseudomonas putida" should read --Pseudomonas mendocina--.

Column 9, line 6, delete "natural of" and insert in place thereof --natural or--; and line 46 where "Pseudomonas putida" should read --Pseudomonas mendocina--.

Column 11, line 40, delete "dodecylsulfate" and insert in place thereof --dodecyl sulfate--; and line 55, where the phrase --$^a$ 0.16 mg/ml cutinase, $^b$ SDS = sodium dodecyl sulfate-- should be inserted after Table II.

Column 12, after line 15, where the phrase-- a= 0.16 mg/ml cutinase--should be inserted after Table IV; line 44, delete "EXAMPLE 8" and insert in place thereof --EXAMPLE 7--; line 46, delete "rinse" and insert in place thereof --rinsed--; and line 49, where "Aspergillus" should read --Aspergillus--.

Column 13, line 34, where "Triton TM, Span TM, Tween TM" should read --Triton$^{TM}$, Span$^{TM}$, Tween$^{TM}$--.

UNITED STATES PATENT AND TRADEMARK OFFICE
CERTIFICATE OF CORRECTION

PATENT NO. : 5,037,662

DATED : August 6, 1991

INVENTOR(S) : Ayrookaran J. Poulose and Matthew Boston

It is certified that error appears in the above-identified patent and that said Letters Patent is hereby corrected as shown below:

Column 14, line 15, where "Triton TM, Span TM, Tween TM" should read --Triton$^{TM}$, Span$^{TM}$, Tween$^{TM}$--; and lines 24 and 25, where "Pseudomonas mendocina" should read --<u>Pseudomonas mendocina</u>--.

Column 15, line 8, where "Triton TM, Span TM, Tween TM" should read --Triton$^{TM}$, Span$^{TM}$, Tween$^{TM}$--.

Column 16, lines 5 and 6, where "Pseudomonas mendorina" should read --<u>Pseudomonas mendocina</u>--.

Signed and Sealed this

Twenty-first Day of June, 1994

*Attest:*

BRUCE LEHMAN

*Attesting Officer*     *Commissioner of Patents and Trademarks*